(12) United States Patent
Paz Rojas et al.

(10) Patent No.: US 9,714,947 B2
(45) Date of Patent: Jul. 25, 2017

(54) CELL BASED SENSOR

(75) Inventors: Elier Paz Rojas, Córdoba (ES); Fé Isabel García Maceira, Córdoba (ES); Verónica Inmaculada Luna Guerrero, Córdoba (ES); María Gracia Montero Peñalvo, Córdoba (ES); Tania García Maceira, Córdoba (ES); José Andrés Morales Martínez, Córdoba (ES); Ana Belén Aragón Gómez, Córdoba (ES); Ana Quesada Molina, Córdoba (ES); Aurora María Márquez Morales, Córdoba (ES)

(73) Assignee: CANVAX BIOTECH S.L., Córdoba (ES)

( * ) Notice: Subject to any disclaimer, the term of this patent is extended or adjusted under 35 U.S.C. 154(b) by 237 days.

(21) Appl. No.: 14/375,334

(22) PCT Filed: Jan. 31, 2012

(86) PCT No.: PCT/EP2012/051530
§ 371 (c)(1),
(2), (4) Date: Oct. 23, 2014

(87) PCT Pub. No.: WO2013/113369
PCT Pub. Date: Aug. 8, 2013

(65) Prior Publication Data
US 2015/0260724 A1    Sep. 17, 2015

(51) Int. Cl.
*G01N 33/58*    (2006.01)
*G01N 33/50*    (2006.01)

(52) U.S. Cl.
CPC ....... *G01N 33/581* (2013.01); *G01N 33/5044* (2013.01); *G01N 2333/726* (2013.01); *G01N 2333/916* (2013.01); *G01N 2333/924* (2013.01); *G01N 2500/02* (2013.01)

(58) Field of Classification Search
CPC ............. G01N 33/581; G01N 33/5044; G01N 2333/726; G01N 2333/916; G01N 2333/924; G01N 2500/02
See application file for complete search history.

(56) References Cited

PUBLICATIONS

International Search Report, Nov. 5, 2012.
Nanamori, Masakatsu, et al.; "A Novel Nonpeptide Ligand for Formyl Peptide Receptor-Like 1," Molecular Pharmacology, 2004, pp. 1213-1222, vol. 66.
Tiberghien, Francoise, et al.; "The MultiScreen® filtration system to measure chemoattractant-induced release of leukocyte granule enzymes by differentiated HL-60 cells or normal human monocytes," Journal of Immunological Methods, 1999, pp. 63-75, vol. 223.

*Primary Examiner* — Ruixiang Li
(74) *Attorney, Agent, or Firm* — Tristan A. Fuierer; Moore & Van Allen, PLLC

(57) ABSTRACT

Cell based sensor. The present invention relates to a novel cell based sensor useful for drug discovery that comprises a cell line with professional regulated exocytosis of secretory granules transfected with a non-protease hydrolase as a reporter polypeptide stored in the regulated secretory granules of the cell line with professional regulated exocytosis and having either an endogenous or a heterologous molecule as a modulator of regulated secretory granules exocytosis. Said granule stored non protease-hydrolase reporter having at least: a high resistance to conditions already present inside the granules such as low pH and proteolysis by other proteases; enzymatic activity after exocytosis; a highly specific substrate; absence of toxicity when cell thawing; a very low level of secretion under unstimulated or basal conditions; and a high signal to background activity in a media compatible with cell culture viability and granule exocytosis for a high throughput robust and sensitive detection.

15 Claims, 3 Drawing Sheets

(A)

(B)

SEQUENCE LISTING

<160> NUMBER OF SEQ ID NOS: 7

<210> SEQ ID NO 1
<211> LENGTH: 1560
<212> TYPE: DNA
<213> ORGANISM: Artificial Sequence
<220> FEATURE:
<223> OTHER INFORMATION: Synthetic Construct

<400> SEQUENCE: 1
atgctgctgc tgctgctgct gctgggcctg aggctacagc tctccctggg catcatccca      60

| | | | |
|---|---|---|---|
| gttgaggagg | agaacccgga | cttctggaac cgcgaggcag ccgaggccct gggtgccgcc | 120 |
| aagaagctgc | agcctgcaca | gacagccgcc aagaacctca tcatcttcct gggcgatggg | 180 |
| atggggtgt | ctacggtgac | agctgccagg atcctaaaag ggcagaagaa ggacaaactg | 240 |
| gggcctgaga | tacccctggc | catgaccgc ttcccatatg tggctctgtc caagacatac | 300 |
| aatgtagaca | acatgtgcc | agacagtgga gccacagcca cggcctacct gtgcggggtc | 360 |
| aagggcaact | tccagaccat | tggcttgagt gcagccgccc gctttaacca gtgcaacacg | 420 |
| acacgcggca | acgaggtcat | ctccgtgatg aatcgggcca agaaagcagg gaagtcagtg | 480 |
| ggagtggtaa | ccaccacacg | agtgcagcac gcctcgccag ccggcaccta cgcccacacg | 540 |
| gtgaaccgca | actggtactc | ggacgccgac gtgcctgcct cggcccgcca ggaggggtgc | 600 |
| caggacatcg | ctacgcagct | catctccaac atggacattg acgtgatcct aggtggaggc | 660 |
| cgaaagtaca | tgtttcgcat | gggaaccccca gaccctgagt acccagatga ctacagccaa | 720 |
| ggtgggacca | ggctggacgg | gaagaatctg gtgcaggaat ggctggcgaa cgccagggt | 780 |
| gcccggtatg | tgtggaaccg | cactgagctc atgcaggctt ccctggaccc gtctgtgacc | 840 |
| catctcatgg | gtctctttga | gcctggagac atgaaatacg agatccaccg agactccaca | 900 |
| ctggacccct | ccctgatgga | gatgacagag ctgccctgc cctgctgag caggaacccc | 960 |
| cgcggcttct | tcctcttcgt | ggagggtggt cgcatcgacc atggtcatca tgaaagcagg | 1020 |
| gcttaccggg | cactgactga | gacgatcatg ttcgacgacg ccattgagag ggcgggccag | 1080 |
| ctcaccagcg | aggaggacac | gctgagcctc gtcactgccg accactccca cgtcttctcc | 1140 |
| ttcggaggct | accccctgcg | agggagctcc atcttcgggc tggcccctgg caaggcccgg | 1200 |
| gacaggaagg | cctacacggt | cctcctatac ggaaacggtc caggctatgt gctcaaggac | 1260 |
| ggcgcccggc | cggatgttac | cgagagcgag agcgggagcc ccgagtatcg gcagcagtca | 1320 |
| gcagtgcccc | tggacgaaga | gacccacgca ggcgaggacg tggcggtgtt cgcgcgcggc | 1380 |
| ccgcaggcgc | acctggttca | cggcgtgcag gagcagacct tcatagcgca cgtcatggcc | 1440 |
| ttcgccgcct | gcctggagcc | ctacaccgcc tgcgacctgg cgccccccgc cggcaccacc | 1500 |
| gacgccgcgc | acccgggtta | ctctagagtc ggggcggccg ccgcttcga gcagacatga | 1560 |

<210> SEQ ID NO 2
<211> LENGTH: 1254
<212> TYPE: DNA
<213> ORGANISM: Artificial Sequence
<220> FEATURE:
<223> OTHER INFORMATION: Synthetic Construct

<400> SEQUENCE: 2

| | | | |
|---|---|---|---|
| atgcaaccaa | tcctgcttct | gctggccttc ctcctgctgc ccagggcaga tgcagggag | 60 |
| atcatcgggg | gacatgaggc | caagcccccac tcccgcccct acatggctta tcttatgatc | 120 |
| tgggatcaga | agtctctgaa | gaggtgcggt ggcttcctga tacaagacga cttcgtgctg | 180 |
| acagctgctc | actgttgggg | aagctccata aatgtcacct tgggggccca caatatcaaa | 240 |
| gaacaggagc | cgacccagca | gtttatccct gtgaaaagac ccatccccca tccagcctat | 300 |
| aatcctaaga | acttctccaa | cgacatcatg ctactgcagc tggagagaaa ggccaagcgg | 360 |
| accagagctg | tgcagcccct | caggctacct agcaacaagg cccaggtgaa gccagggcag | 420 |
| acatgcagtg | tggccggctg | ggggcagacg gcccccctgg aaaacactc acacacacta | 480 |
| caagaggtga | agatgacagt | gcaggaagat cgaaagtgcg aatctgactt acgccattat | 540 |

| tacgacagta ccattgagtt gtgcgtgggg gacccagaga ttaaaaagac ttcctttaag | 600 |
| ggggatgctg gagggcccct tgtgtgtaac aaggtggccc agggcattgt ctcctatgga | 660 |
| cgaaacaatg gcatgcctcc acgagcctgc accaaagtct caagctttgt acactggata | 720 |
| aagaaaacca tgaaacgcta caccggtaag ccaacagaga caatgaggga cttcaacatc | 780 |
| gtggccgtgg caagcaactt cgccacaacc gacctggatg ctgacagggg caagttgccc | 840 |
| ggaaagaagc tgcccctgga ggtgctgaag gagatgagg ccaacgccag gaaggctggc | 900 |
| tgcaccaggg gctgtctgat ctgcctgtcc cacatcaagt gcacccccaa gatgaagaag | 960 |
| ttcatcccag gaagatgcca cacctacgag ggagacaagg agagcgccca gggcggcatc | 1020 |
| ggagaggcca tcgtggacat ccctgagatc cccggcttca aggacctgga gcccatggag | 1080 |
| cagttcatcg cccaggtgga cctgtgcgtg gactgcacca ccggctgcct gaagggcctg | 1140 |
| gccaacgtgc agtgctccga tctgctgaag aagtggctgc cccagagatg cgccaccttc | 1200 |
| gccagcaaga tccagggcca ggtggacaag atcaagggcg ccggcggcga ctaa | 1254 |

<210> SEQ ID NO 3
<211> LENGTH: 1205
<212> TYPE: DNA
<213> ORGANISM: Artificial Sequence
<220> FEATURE:
<223> OTHER INFORMATION: Synthetic Construct

<400> SEQUENCE: 3

| ttgctgactt gcgtgaggct ccggtgcccg tcagtgggca gagcgcacat cgcccacagt | 60 |
| ccccgagaag ttgggggggag gggtcggcaa ttgaaccggt gcctagagaa ggtggcgcgg | 120 |
| ggtaaactgg gaaagtgatg tcgtgtactg gctccgcctt tttcccgagg gtgggggaga | 180 |
| accgtatata agtgcagtag tcgccgtgaa cgttctttt cgcaacgggt ttgccgccag | 240 |
| aacacaggta agtgccgtgt gtggttcccg cgggcctggc ctctttacgg gttatggccc | 300 |
| ttgcgtgcct tgaattactt ccacgcccct ggctgcagta cgtgattctt gatcccgagc | 360 |
| ttcgggttgg aagtgggtgg gagagttcga ggccttgcgc ttaaggagcc ccttcgcctc | 420 |
| gtgcttgagt tgaggcctgg cctgggcgct ggggccgccg cgtgcgaatc tggtggcacc | 480 |
| ttcgcgcctg tctcgctgct ttcgataagt ctctagccat ttaaaatttt tgatgacctg | 540 |
| ctgcgacgct tttttctgg caagatagtc ttgtaaatgc gggccaagat ctgcacactg | 600 |
| gtatttcggt ttttggggcc gcgggcggcg acggggcccg tgcgtcccag cgcacatgtt | 660 |
| cggcgaggcg gggcctgcga gcgcggccac cgagaatcgg acggggtag tctcaagctg | 720 |
| gccggcctgc tctggtgcct ggcctcgcgc cgccgtgtat cgccccgccc tgggcggcaa | 780 |
| ggctggcccg tcggcacca gttgcgtgag cggaaagatg gccgcttccc ggccctgctg | 840 |
| cagggagctc aaaatggagg acgcggcgct cgggagagcg ggcgggtgag tcacccacac | 900 |
| aaaggaaaag ggccttttcg tcctcagccg tcgcttcatg tgactccacg gagtaccggg | 960 |
| cgccgtccag gcacctcgat tagttctcga gcttttggag tacgtcgtct ttaggttggg | 1020 |
| gggagggtt ttatgcgatg gagtttcccc acactgagtg ggtggagact gaagttaggc | 1080 |
| cagcttggca cttgatgtaa ttctccttgg aatttgccct ttttgagttt ggatcttggt | 1140 |
| tcattctcaa gcctcagaca gtggttcaaa gttttttct tccatttcag gtgtcgtgct | 1200 |
| agctt | 1205 |

<210> SEQ ID NO 4
<211> LENGTH: 479

<212> TYPE: DNA
<213> ORGANISM: Artificial Sequence
<220> FEATURE:
<223> OTHER INFORMATION: Synthetic Construct

<400> SEQUENCE: 4

```
agtctccaga aaaaggggggg aatgaaagac cccacctgta ggtttggcaa gctagcttaa      60
gtaacgccat tttgcaaggc atggaaaaat acataactga aatagagaa gttcagatca       120
aggtcaggaa cagatggaac agctgaatat gggccaaaca ggatatctgt ggtaagcagt     180
tcctgccccg gctcagggcc aagaacagat ggaacagctg aatatgggcc aaacaggata    240
tctgtggtaa gcagttcctg ccccggctca gggccaagaa cagatggtcc ccagatgcgg    300
tccagccctc agcagtttct agagaaccat cagatgtttc cagggtgccc caaggacctg    360
aaatgaccct gtgccttatt tgaactaacc aatcagttcg cttctcgctt ctgttcgcgc    420
gcttctgctc cccgagctca ataaaagagc ccacaacccc tcactcgggg cgccagtcc     479
```

<210> SEQ ID NO 5
<211> LENGTH: 105
<212> TYPE: DNA
<213> ORGANISM: Artificial Sequence
<220> FEATURE:
<223> OTHER INFORMATION: Synthetic Construct

<400> SEQUENCE: 5

```
ctgagcacaa tggccccagg ctccaccgtg gaacactcg atgccaacat gaccagcgtg       60
aatgccacag aggacgcctg caccaagagc tacagcgcct cctc                      105
```

<210> SEQ ID NO 6
<211> LENGTH: 36
<212> TYPE: DNA
<213> ORGANISM: Artificial Sequence
<220> FEATURE:
<223> OTHER INFORMATION: Synthetic Construct

<400> SEQUENCE: 6

```
ctgagcacaa tggccccagg ctccaccgtg ggaaca                               36
```

<210> SEQ ID NO 7
<211> LENGTH: 5348
<212> TYPE: DNA
<213> ORGANISM: Artificial Sequence
<220> FEATURE:
<223> OTHER INFORMATION: Synthetic Construct

<400> SEQUENCE: 7

```
gacggatcgg gagatctccc gatccctat ggtgcactct cagtacaatc tgctctgatg       60
ccgcatagtt aagccagtat ctgctccctg cttgtgtgtt ggaggtcgct gagtagtgcg    120
cgagcaaaat ttaagctaca caaggcaag gcttgaccga caattgcatg aagaatctgc    180
ttagggttag gcgttttgcg ctgcttcgt atatcgaatt cagtctccag aaaaggggg    240
gaatgaaaga cccacctgt aggtttggca agctagctta agtaacgcca ttttgcaagg    300
catggaaaaa tacataactg aatagagaa agttcagatc aaggtcagga acagatggaa    360
cagctgaata tgggccaaac aggatatctg tggtaagcag ttcctgcccc ggctcagggc    420
caagaacaga tggaacagct gaatatgggc caaacaggat atctgtggta agcagttcct    480
gccccggctc agggccaaga acagatggtc cccagatgcg gtccagccct cagcagtttc    540
tagagaacca tcagatgttt ccagggtgcc ccaaggacct gaaatgaccc tgtgccttat    600
```

```
ttgaactaac caatcagttc gcttctcgct tctgttcgcg cgcttctgct ccccgagctc    660
aataaaagag cccacaaccc ctcactcggg gcgccagtcc aagcttggta ccgagctcgg    720
atcgatcatg gagacagaca cactcctgct atgggtactg ctgctctggg ttccaggttc    780
caccggtgac gaacaaaaac tcatctcaga gaggatctg gggccatcgc gactgagcac     840
aatggcccca ggctccaccg tgggaacact cgagggatcc gcggccgctc tagagggccc    900
tattctatag tgtcacctaa atgctagagc tcgctgatca gcctcgactg tgccttctag    960
ttgccagcca tctgttgttt gcccctcccc cgtgccttcc ttgaccctgg aaggtgccac   1020
tcccactgtc ctttcctaat aaaatgagga aattgcatcg cattgtctga gtaggtgtca   1080
ttctattctg ggggtgggg tggggcagga cagcaagggg gaggattggg aagacaatag    1140
caggcatgct ggggatgcgg tgggctctat ggcttctgag gcggaaagaa ccagctgggg   1200
ctctaggggg tatccccacg cgccctgtag cggcgcatta agcgcggcgg gtgtggtggt   1260
tacgcgcagc gtgaccgcta cacttgccag cgccctagcg cccgctcctt tcgctttctt   1320
cccttccttt ctcgccacgt tcgccggctt tccccgtcaa gctctaaatc ggggctccc    1380 tttagggttc cgatttagtg ctttacggca cctcgacccc aaaaaacttg attagggtga   1440
tggttcacgt agtgggccat cgccctgata gacggttttt cgccctttga cgttggagtc   1500
cacgttcttt aatagtggac tcttgttcca actggaaca acactcaacc ctatctcggt    1560
ctattctttt gatttataag ggattttgcc gatttcggcc tattggttaa aaaatgagct   1620
gatttaacaa aaatttaacg cgaattaatt ctgtggaatg tgtgtcagtt agggtgtgga   1680
aagtccccag gctcccagc aggcagaagt atgcaaagca tgcatctcaa ttagtcagca    1740
accaggtgtg gaaagtcccc aggctcccca gcaggcagaa gtatgcaaag catgcatctc   1800
aattagtcag caaccatagt cccgccccta actccgccca tcccgcccct aactccgccc   1860
agttccgccc attctccgcc ccatggctga ctaatttttt ttatttatgc agaggccgag   1920
gccgcctctg cctctgagct attccagaag tagtgaggag gcttttttgg aggcctaggc   1980
ttttgcaaaa agctcccggg agcttgtata tccattttcg gatctgatca agagacagga   2040
tgaggatcgt ttcgcatgat tgaacaagat ggattgcacg caggttctcc ggccgcttgg   2100
gtggagaggc tattcggcta tgactgggca caacagacaa tcggctgctc tgatgccgcc   2160
gtgttccggc tgtcagcgca ggggcgcccg gttcttttg tcaagaccga cctgtccggt    2220
gccctgaatg aactgcagga cgaggcagcg cggctatcgt ggctggccac gacgggcgtt   2280
ccttgcgcag ctgtgctcga cgttgtcact gaagcgggaa gggactggct gctattgggc   2340
gaagtgccgg ggcaggatct cctgtcatct caccttgctc ctgccgagaa agtatccatc   2400
atggctgatg caatgcggcg gctgcatacg cttgatccgg ctacctgccc attcgaccac   2460
caagcgaaac atcgcatcga gcgagcacgt actcggatgg aagccggtct tgtcgatcag   2520
gatgatctgg acgaagagca tcaggggctc gcgccagccg aactgttcgc caggctcaag   2580
gcgcgcatgc ccgacggcga ggatctcgtc gtgacccatg gcgatgcctg cttgccgaat   2640
atcatggtgg aaaatggccg cttttctgga ttcatcgact gtggccggct gggtgtggcg   2700
gaccgctatc aggacatagc gttggctacc cgtgatattg ctgaagagct tggcggcgaa   2760
tgggctgacc gcttcctcgt gctttacggt atcgccgctc ccgattcgca gcgcatcgcc   2820
ttctatcgcc ttcttgacga gttcttctga gcgggactct ggggttcgaa atgaccgacc   2880
aagcgacgcg caacctgcca tcacgagatt tcgattccac cgccgccttc tatgaaaggt   2940
tgggcttcgg aatcgttttc cgggacgccg gctggatgat cctccagcgc ggggatctca   3000
```

```
tgctggagtt cttcgcccac cccaacttgt ttattgcagc ttataatggt tacaaataaa     3060
gcaatagcat cacaaatttc acaaataaag catttttttc actgcattct agttgtggtt     3120
tgtccaaact catcaatgta tcttatcatg tctgtatacc gtcgacctct agctagagct     3180
tggcgtaatc atggtcatag ctgtttcctg tgtgaaattg ttatccgctc acaattccac     3240
acaacatacg agccggaagc ataaagtgta aagcctgggg tgcctaatga gtgagctaac     3300
tcacattaat tgcgttgcgc tcactgcccg ctttccagtc gggaaacctg tcgtgccagc     3360
tgcattaatg aatcggccaa cgcgcgggga gaggcggttt gcgtattggg cgctcttccg     3420
cttcctcgct cactgactcg ctgcgctcgg tcgttcggct gcggcgagcg gtatcagctc     3480
actcaaaggc ggtaatacgg ttatccacag aatcagggga taacgcagga aagaacatgt     3540
gagcaaaagg ccagcaaaag gccaggaacc gtaaaaaggc cgcgttgctg gcgttttcc      3600 ataggctccg cccccctgac gagcatcaca aaaatcgacg ctcaagtcag aggtggcgaa     3660
acccgacagg actataaaga taccaggcgt ttccccctgg aagctccctc gtgcgctctc     3720
ctgttccgac cctgccgctt accggatacc tgtccgcctt tctcccttcg ggaagcgtgg     3780
cgctttctca tagctcacgc tgtaggtatc tcagttcggt gtaggtcgtt cgctccaagc     3840
tgggctgtgt gcacgaaccc cccgttcagc ccgaccgctg cgccttatcc ggtaactatc     3900
gtcttgagtc aacccggta agacacgact tatcgccact ggcagcagcc actggtaaca     3960
ggattagcag agcgaggtat gtaggcggtg ctacagagtt cttgaagtgg tggcctaact     4020
acggctacac tagaagaaca gtatttggta tctgcgctct gctgaagcca gttaccttcg     4080
gaaaaagagt tggtagctct tgatccggca acaaaccac cgctggtagc ggttttttg      4140 tttgcaagca gcagattacg cgcagaaaaa aaggatctca agaagatcct ttgatctttt     4200 ctacgggtc tgacgctcag tggaacgaaa actcacgtta agggattttg gtcatgagat     4260
tatcaaaaag gatcttcacc tagatccttt taaattaaaa atgaagtttt aaatcaatct     4320
aaagtatata tgagtaaact tggtctgaca gttaccaatg cttaatcagt gaggcaccta     4380
tctcagcgat ctgtctattt cgttcatcca tagttgcctg actccccgtc gtgtagataa     4440
ctacgatacg ggagggctta ccatctggcc ccagtgctgc aatgataccg cgagacccac     4500
gctcaccggc tccagattta tcagcaataa accagccagc cggaagggcc gagcgcagaa     4560
gtggtcctgc aactttatcc gcctccatcc agtctattaa ttgttgccgg gaagctagag     4620
taagtagttc gccagttaat agtttgcgca acgttgttgc cattgctaca ggcatcgtgg     4680
tgtcacgctc gtcgtttggt atggcttcat tcagctccgg ttcccaacga tcaaggcgag     4740
ttacatgatc ccccatgttg tgcaaaaaag cggttagctc cttcggtcct ccgatcgttg     4800
tcagaagtaa gttggccgca gtgttatcac tcatggttat ggcagcactg cataattctc     4860
ttactgtcat gccatccgta agatgctttt ctgtgactgg tgagtactca accaagtcat     4920
tctgagaata gtgtatgcgg cgaccgagtt gctcttgccc ggcgtcaata cgggataata     4980
ccgcgccaca tagcagaact ttaaaagtgc tcatcattgg aaaacgttct cggggcgaa      5040 aactctcaag gatcttaccg ctgttgagat ccagttcgat gtaacccact cgtgcaccca     5100
actgatcttc agcatctttt actttcacca gcgtttctgg gtgagcaaaa acaggaaggc     5160
aaaatgccgc aaaaaaggga ataagggcga cacggaaatg ttgaatactc atactcttcc     5220
```

```
tttttcaata ttattgaagc atttatcagg gttattgtct catgagcgga tacatatttg    5280
aatgtattta gaaaaataaa caaatagggg ttccgcgcac atttccccga aaagtgccac    5340
ctgacgtc                                                              5348
```

CELL BASED SENSOR

CROSS-REFERENCE TO RELATED APPLICATIONS

This application is filed under the provisions of 35 U.S.C. §371 and claims the priority of International Patent Application No. PCT/EP2012/051530 filed on 31 Jan. 2012 entitled "CELL BASED SENSOR" in the name of Elier PAZ ROJAS, et al., which is hereby incorporated by reference herein in its entirety.

FIELD OF THE INVENTION

The present invention is comprised in the biotechnological and pharmaceutical field. It refers to a cell based sensor useful for drug discovery, diagnostic and determination of analytes that comprises a cell line with professional regulated exocytosis of secretory granules overexpressing a non-protease hydrolase selected, preferably, from a group comprising a *Gaussia* luciferase fusion protein with a granule targeting protein, a secretable alkaline phosphatase and a chain beta of beta-hexosaminidase, as possible reporter polypeptides, stored in the regulated secretory granules of the cell line with professional regulated exocytosis, and having either an endogenous or a heterologous molecule as a modulator of regulated secretory granules exocytosis, such said granule stored non protease-hydrolase reporter having at least: a high resistance to conditions already present inside the granules such as low pH and proteolysis by proteases; enzymatic activity after exocytosis; absence of toxicity, specially after cell thawing; a highly specific substrate; a very low level of secretion under unstimulated or basal conditions; and a high signal to background activity in a media compatible with cell culture viability and granule exocytosis for a high throughput robust and sensitive detection.

When the cell based sensor is incubated with a specific ligand of the exocytosis modulator the reporter polypeptide is released from granules into the extracellular media and the enzymatic activity of such released non-protease hydrolase reporter polypeptide is detected with a specific substrate.

Such sensitive cell based sensor is useful for testing interactions between at least two molecules, one acting as the exocytosis modulator and the other as the specific ligand of the exocytosis modulator. Examples of uses of such sensors are: to test interactions between molecules in drug discovery, to quantify molecules such as proteins or volatile organic compounds for diagnostic and for detection of drugs or molecules in several samples for example in the food industry, in environmental samples and in the pharmaceutical industry.

STATE OF THE ART

The G-protein coupled receptor (GPCR) superfamily represents the single largest slice of the over than 1000 surface receptors that are expressed on the membrane of eukaryotic cells.

GPCRs are central for cell communication with their extracellular media, but also for vision, taste and olfaction. Thus, methods to measure and/or quantify activation or inhibition of activity GPCRs by compounds are central for drug discovery and also for diagnostic of diseases.

Exocytosis by hematopoietic cells with professional regulated exocytosis is very well-known in the state of the art and also exocytosis induced by agonist binding to GPCRs. But such exocytosis is always measured as a percentage because there is a strong variability in the amount of enzyme stored into the granules of cells, for example in the amount of beta-hexosaminidase. In order to determine a percentage of exocytosis a first measure is made to quantify the amount of ligand-induced release of the granule stored enzyme after binding of ligand and receptor and then cells are lysed with detergents, incubated again and total enzyme stored inside the cells is determined. Background of unstimulated cells is subtracted from both ligand induced release and total release and then percentage of exocytosis is the ratio between specific release with ligand and total specific release. But this determination of percentage of release has several steps that increase the cost of assays, increase the assay time and thus reduce throughput. Also, the percentage of exocytosis is in many cases very low and thus this assay has low sensitivity.

It has been previously demonstrated in PCT/EP2010/004619 by the inventors of present patent application, that certain proteases such as human granzyme B may be overexpressed inside such granules of hematopoietic cells with professional exocytosis, that such assay has an improved signal-to-background ratio and that there is a stable production of the protease inside the granules so that percentage of exocytosis is not needed to compare exocytosis between two experiments. As cited in PCT/EP2010/004619, the most widely used reporter for granule secretion is endogenous beta-hexosaminidase but this protein has been traditionally considered a low sensitivity reporter with a low signal to background ratio and a strong variability between experiments due to a large variation over time in the amount of enzyme stored in the granules. Consequently, although PCT/EP2010/004619 discloses the possible use of beta-hexosaminidase as reporter, it cannot be considered an enabling disclosure for the present invention because the teachings of PCT/EP2010/004619 do not enable the skilled person in the art to use of beta-hexosaminidase as reporter because, in fact, the disclosure made in that prior art, it did teach away from said use explaining why beta-hexosaminidase is not a reliable reporter. Moreover, in present invention, beta-hexoaminidase is not used as such as reporter, but only the chain beta of the enzyme and overexpressed.

In addition, overexpression of proteases such as granzyme B inside the granules of hematopoietic cells is toxic for cells, in particular after thawing of cells, where about 30-40 percent of the cells were died 24 hours after thawing.

The present invention is focused on the development of a cell based sensor, comprising reporters which are different to the reporters used in the cell based sensor which are known in the prior art.

DESCRIPTION OF THE INVENTION

Brief Description of the Invention

The present invention overcomes the above cited problems demonstrating that other hydrolases, which are not proteases, are not toxic when overexpressed inside granules of thawed cells and that they allow the development of highly sensitive sensors. In particular, certain glycosidases such as the chain B of beta-hexosaminidase and phosphatases such as secretable alkaline phosphatase are stored in high levels inside granules of hematopoietic cells with professional regulated exocytosis and are detected by ligand induced exocytosis with a high signal to background ratio and with low interassay variability. In addition, the present invention also demonstrates that the above invention's specific embodiments can be generalized to other non protease-hydrolases not normally stored inside the granules that may be redirected to granules by means of granule targeting polypeptides. For example, *Gaussia* luciferase is a non protease-hydrolase not normally stored inside granules that can be redirected to granule by means of a granule targeting polypeptide such as granzyme B, overexpressed and stored into the granules and released like beta-hexosaminidase by a ligand induced exocytosis. Thus, hematopoietic cells over-expressing non toxic non protease-hydrolases become sensitive cell-based sensors with low variability to measure exocytosis.

The following terms are defined for the purpose of the present invention:

Sensor: Is a type of transducer. Transducer is defined as any device that converts a signal from one form to another. Sensors that transduce a biological signal are called biosensors.

Regulated exocytosis: It refers to a process where specialized cells secrete neurotransmitters, hormones, enzymes, peptides or low molecular weight substances (e.g. catecholamines, glutamate, etc). Normally a rise in intracellular Ca2+ concentration is the trigger for exocytosis but there are other intracellular signals including cAMP, diacylglycerol (DAG), phospholipids, and ATP that also regulate or modulate Ca2+-triggered exocytosis. Cells with professional regulated exocytosis refers to cells that normally store metabolites or polypeptides inside their granules and release such granule-stored metabolites or polypeptides upon an extracellular signal.

Secretory granules or secretory vesicles or secretory lysosomes: They are specialized intracellular organelles that serve as a storage pool for selected secretory products. Secretory granules move towards the periphery of the cell by a stimulus or a modulator, their membranes fuse with the cell membrane, and their content load is released. Although in most cell types, secretory granules appear to represent an entirely new class of organelle, granules in various hematopoietic cells and certain other cell types share several properties with lysosomes.

Hematopoietic cell: They are cells derived from bone marrow stem cells and comprises all the blood cell types that include both the myeloid (monocytes and macrophages, neutrophils, basophils, eosinophils, erythrocytes, megakaryocytes/platelets and some dendritic cells) and lymphoid lineages (T-cells, B-cells, NK-cells, some dendritic cells).

Cell line with regulated exocytosis: As used herein, the terms "cell with regulated exocytosis," "professional secretory cell line," and "cell line with professional regulated exocytosis" may be used interchangeably. For the methods of the present invention important cell lines are hematopoietic cell lines with professional regulated exocytosis.

Reporter polypeptide or reporter: It is a gene that researchers attach to another gene of interest in cell culture, animals or plants. Certain genes are chosen as reporters because the characteristics they confer on organisms expressing them are easily identified and measured, or because they are selectable markers. Reporter genes are generally used to determine whether the gene of interest has been taken up by or expressed in the cell or organism population. Reporter genes herein are polypeptides stored inside secretory granules of professional secretory cell lines like certain hematopoietic cells and are released into the extracellular media by a stimulus or a modulator of exocytosis.

Granule targeting polypeptide: It is a polypeptide that is naturally stored inside the granules of cells with regulated exocytosis. Such polypeptides contain both known and unknown sequences that target proteins to granules. Examples of such granule targeting polypeptides comprise beta-hexosaminidase, p-selectin, granzymes such as A, B, M, H, K, cathepsins. Proteins not normally stored into granules may be stored into granules by making a fusion protein with granule targeting polypeptides. In the present invention we use the term "redirected" to describe the fact that a protein not normally stored into granules may be fused with another and the resultant protein may be stored also into granules.

Hydrolase: It is an enzyme that catalyzes the hydrolysis of a chemical bond. Hydrolases are classified in the group 3 in the EC number classification of enzymes and can be further classified into several subclasses, based upon the bonds they act upon: esterases that cleave an esther bond such as nucleases, phosphodiesterases, lipase, phosphatase; glycosylases that cleave sugars and proteases, comprising granzymes, or peptidases that cleave a peptide bond.

Non-Protease hydrolase: It is an enzyme that catalyzes the hydrolysis of a chemical bond, other than a peptide bond.

Modulator of regulated exocytosis: It refers to a compound, molecule, or composition that is capable of altering one or more signal transduction pathways downstream involved in regulated exocytosis process. This alteration in activity encompasses inhibition (i.e., the compound, molecule or composition is an "inhibitor" of exocytosis), as well as stimulation, induction or enhancement (i.e., the compound, molecule or composition is a "stimulator", "inductor" or "enhancer" of exocytosis). These modulators are identified using in vitro and/or in vivo assays. In these assays, controls are used in order to permit comparisons between samples.

Drug discovery: It refers to a process by which drugs are discovered and/or designed. As used herein drug discovery comprises drug identification and modifications for affinity, side effects, bioavailability but also testing the effect of a drug previously launched to the market in a new therapeutic indication, a process also known as reprofiling.

Gene: It is the fundamental physical and functional unit of heredity. In biochemical terms, a gene is an ordered sequence of nucleotides located in a particular position on a particular chromosome that encodes a specific functional product (i.e., a protein or RNA molecule). As used herein, a gene is composed not only of coding sequences but can comprise adjacent DNA regions involved in control of the transcription of the coding sequences (e.g., promoters, enhancers) and introns. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogeneous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

"Stably introduced" or "stably transformed" or "stably transduced" or "stably transfected" or "stably electroporated": It refers to the fraction of cells with the desirable foreign DNA integrated into their genome. Depending upon the expression vector and transfection technique used, only a fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and puromycin. Nucleic acid encoding a selectable marker can be introduced into a host cell on the same vector as that encoding a detectable translation product or can be introduced on a separate vector. Cells stably transfected with the introduced nucleic acid can be identified by drug selection (e.g., cells that have incorporated the selectable marker gene will survive, while the other cells die).

Surface receptor: It refers to molecules that occur on the surface of cells, interact with the extracellular environment and transmit or transduce the information regarding the environment intracellularly in a manner that ultimately modulates transcription of specific promoters, resulting in transcription of specific genes. Examples of surface receptor are tyrosine kinase receptors, ion channel receptors, cytokine receptors, chemokine receptors or a G-protein coupled receptors (GPCRs), such as chemoattractant peptide receptors, neuropeptide receptors, light receptors, neurotransmitter receptors, or polypeptide hormone receptors.

G protein-coupled receptors (GPCRs), also known as seven transmembrane receptors, 7TM receptors, heptahelical receptors, and G protein linked receptors (GPLR): They are a large protein family of transmembrane receptors characterized by seven membrane-spanning domains with an extracellular N terminus and a cytoplasmic C terminus. Ligand binding to GPCRs promotes conformational changes leading to small G-protein coupling, the initiation of signal transduction pathways, and ultimately to cellular responses. The ligands that bind and activate these receptors include light-sensitive compounds, odors, pheromones, hormones, and neurotransmitters, and vary in size from small molecules to peptides to large proteins. G protein-coupled receptors are only found in higher eukaryotes, including yeast, plants, and, especially, animals. G protein-coupled receptors are involved in many diseases, but are also the target of around half of all modern medicinal drugs.

GPCRs: They operate through a similar molecular mechanism. Activation of GPCR by extracellular stimuli causes conformational changes in the receptor, which results in the intermediate coupling and activation of GTP-binding proteins (G proteins). G proteins are heterotrimeric in nature and are composed of alpha ($\alpha$), beta ($\beta$), and gamma ($\gamma$) subunits encoded by distinct genes. The alpha subunit is responsible for the binding of GDP and GTP. Binding of a ligand to a GPCR results in a transition of the alpha ($\alpha$) subunit from a GDP-bound form to a GTP-bound form and leads to the activation of the heterotrimer through dissociation of the $\alpha$-GTP from the $\beta\gamma$ dimer. Both $\alpha$-GTP and the $\beta\gamma$ dimer regulate the activities of a variety of effectors that transmit the signal to the cell interior through the production of second messenger molecules (e.g., calcium, cAMP, etc). There are at least 17 Galpha (G$\alpha$) genes, and members of G proteins can be grouped into four main classes termed G$\alpha$i/$_o$, G$\alpha_{q/11}$, G$\alpha_s$ and G$\alpha_{12/13}$. (see e.g. Preininger A M and Hamm H E. *Sci. STKE* 2004, re3 and Cabrera-Vera T M et al. Endocr Rev. 2003 December; 24(6):765-81. As used herein, a GPCR comprises receptors coupled to either G$\alpha$i/$_o$, G$\alpha_{q/11}$, G$\alpha_s$ and G$\alpha_{12/13}$.

Receptor with intrinsic enzymatic tyrosine kinase activity (RTKs): They are high affinity cell surface receptors for many polypeptide growth factors, cytokines and hormones. Of the ninety unique tyrosine kinase genes identified in the human genome, 58 encode receptor tyrosine kinase proteins. Most RTKs are single subunit receptors but some e.g. the insulin receptor exist as multimeric complexes. Each monomer has a single transmembrane spanning domain, an extracellular N-terminal region and an intracellular C-terminal region. The extracellular N-terminal region is composed of a very large protein domain which binds to extracellular ligands (e.g. a particular growth factor). The intracellular C-terminal region is comprised of regulatory domains and domains responsible for the kinase activity of these receptors, which specifically phosphorylate tyrosine amino acids.

Chimeric receptors: Thy are based on an artificial receptor that combined parts of one receptor with parts of another receptor, protein fragments, tags and any combination thereof, including both entire domains and portions thereof. In general, a chimeric protein or "fusion protein" is a polypeptide comprising at least one portion of the desired protein product fused to at least another peptide sequence or to another polypeptide.

Vector or plasmid vector or plasmid: The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis, et al., Molecular Cloning, A Laboratory Manual (Cold Spring Harbor, 1990) and Ausubel, et al., 1994, Current Protocols In Molecular Biology (John Wiley & Sons, 1996), both incorporated herein by reference).

Expression vector: The term "expression vector" refers to any type of genetic construct comprising a nucleic acid coding for a RNA capable of being transcribed. Expression vectors normally comprise at least a promoter and a poly-A signal. A promoter is a control sequence that is a region of a nucleic acid sequence at which initiation and rate of transcription are controlled. A poly-A signal or termination signal comprises a DNA sequence involved in specific termination of an RNA transcript by an RNA polymerase. A terminator may be necessary in vivo to achieve desirable message levels.

Promoters: Promoters are sequences of DNA that contain regions involved in control of the transcription of the adjacent coding sequences. Specific regulatory DNA sequences located away from the transcriptional start site of promoter are called enhancers. Other sequences of the promoters comprise the TATA box sequence which binds to TATA-binding proteins that assist the formation of the RNA polymerase transcriptional complex. But the relevant sequences have a large variability between different promoters. By comparison of different promoters consensus sequences have been determined. The degree to which a given promoter conforms to the consensus sequence determines the strength of that promoter. The closer the sequence to the consensus, the stronger the promoter will be and the more frequently transcription will occur at that promoter. Promoter strength is important because it determines how often a given mRNA sequence is transcribed, effectively giving higher priority for transcription to some genes over others. A gene that codes for a protein that is required in large quantities, for example, might be expected to have a relatively strong promoter. Thus, the classification of promoters as strong or weak is a relative classification where strong promoters are those transcribed more frequently than weak promoters. Thus, as used herein a strong promoter is one transcribed relatively more frequently than other promoters and that produce higher protein levels than weak promoters. Examples of strong promoters are CMV promoter, Elongation factor 1-alpha promoter and a chimeric promoter between CMV and MoMLV5'LTR promoter.

Overexpression: a protein may be overexpressed in a cell line by using an expression vector to either increase the previously existing levels of a protein in such cell line or to produce large quantities of a protein in such cell line. Usually the expression vectors used for protein overexpression are strong constitutive or strong inducible promoters.

Signal peptide or a signal sequence: A signal peptide is a short (3-60 amino acids long) peptide chain that directs the post-translational transport of a protein. Signal peptides may also be called targeting signals, signal sequences, transit peptides, or localization signals. The amino acid sequences of signal peptides direct proteins (which are synthesized in the cytosol) to certain organelles such as the nucleus, mitochondrial matrix, endoplasmic reticulum, chloroplast, apoplast and peroxisome. Some signal peptides are cleaved from the protein by signal peptidase after the proteins are transported.

Peptide tag: Peptide tags are short peptides that may be used to detect proteins for example with antibodies when specific antibodies to the protein are not available or for protein purification. Examples of known peptide tag that could be used for cell surface detection and separation are c-myc tag, HA tag and FLAG sup.TM tag. In general any peptide tag for which is available a specific binding protein could be used for surface detection and or separation provided such specific binding protein is labeled either directly or indirectly with a fluorophore or for example with a bead for surface separation.

Basal secretion: Basal secretion refers to the relative amount of protein secreted by cells in the absence of a modulator of cell exocytosis. In almost all secretory cell types, a level of basal secretion can be detected. It is not known if basal secretion results from release of protein stored into granules or from a fraction of newly synthesized protein that is sorted away from secretory granules. (see for example Burgoyne R D and Morgan A. Physiol Rev (2003) 83: 581-632).

Recombinant DNA (rDNA) molecule: It refers to a DNA molecule produced by operatively linking a nucleic acid sequence, such as a gene, to a DNA molecule sequence.

Transformation or transfection: It refers, as used herein, to the introduction of foreign DNA into cells (e.g. prokaryotic or eukaryotic cells). Transformation may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics. In particular transfection into eukaryotic cells could be transient when a suitable antibiotic is not included into the cell culture media for selection of cells bearing a stable integration of DNA into the chromosomes. Plasmid vectors for stable selection must have a selectable marker that is expressed into cells that are to be selected with an antibiotic.

Comprising: This term, all along present patent description, includes, specifically, the term "consisting", when referred, particularly, to biological sequences, as amino acid or nucleotide sequences. It is meant that the sequence may either comprise a fragment on which the invention, taken as biological activity or technical effect, mainly resides, optionally jointly to other sequence fragments or sequence parts; or simply, being restricted precisely to the fragment as such.

DETAILED DESCRIPTION OF THE INVENTION

Figure 1:
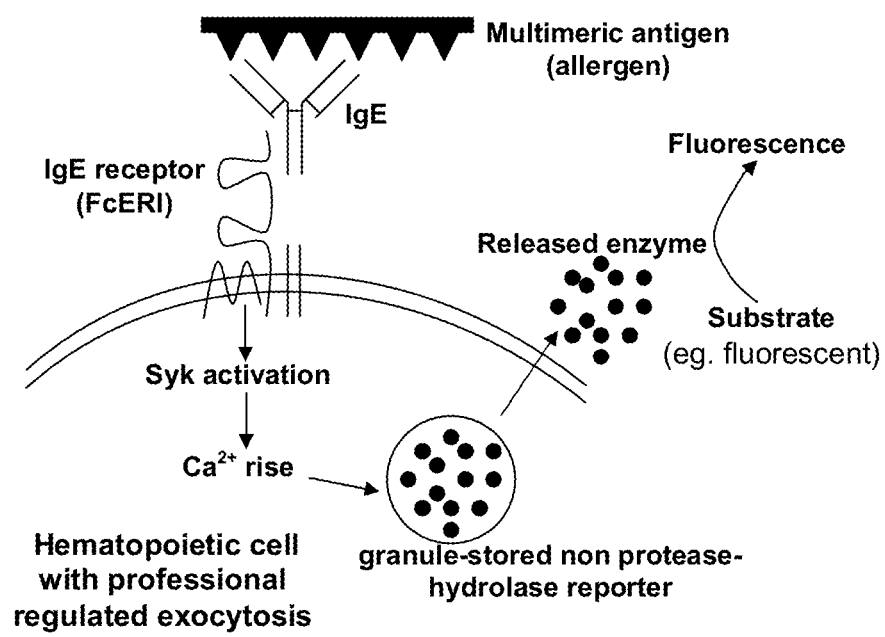
FIG. 1. It shows the general concept of the present invention, using a non protease-hydrolase as a granule stored reporter, the IgE receptor as the cell surface receptor that modulates granule exocytosis and a substrate that is cleaved by secreted granule stored non protease-hydrolase reporter for detection. Treatment of cells with a multimeric antigen (for example, an allergen) that binds to high affinity receptor bound IgE induces release of granule stored non protease-hydrolase and such non protease-hydrolase cleaves the substrate to produce a fluorescent end product. Using this specific substrate of the secreted reporter enzyme, ligand-to-receptor-interation can be determined.
Figure 2:
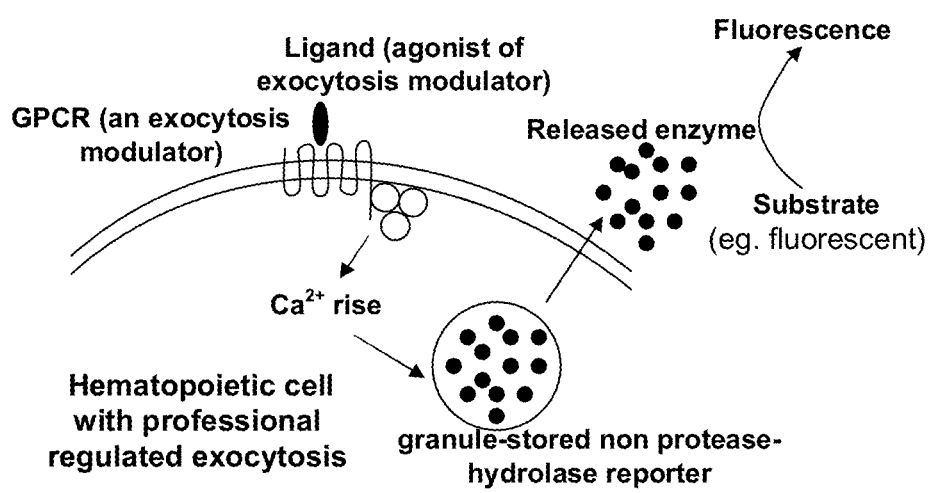
FIG. 2. Drawing of the general concept of the present invention, using a non-protease hydrolase as a granule stored reporter, a GPCR as the cell surface receptor that modulates granule exocytosis and a fluorescent substrate cleaved by secreted granule stored hydrolase reporter for detection. Treatment of cells with an agonist of the GPCR induces release of granule stored hydrolase and such hydrolase cleaves the substrate to produce a fluorescent end product. Using a specific substrate of the secreted reporter enzyme, ligand-to-receptor-interation can be determined.
Figure 3:
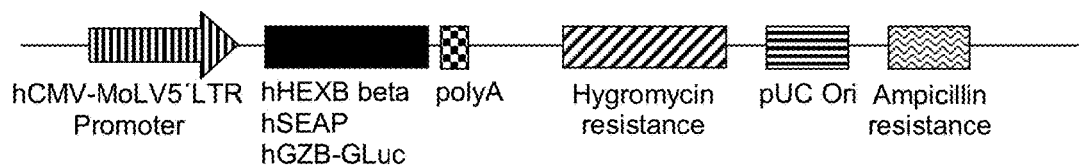
FIG. 3. General structure of representative plasmid vectors of the present invention. Map of the plasmid vector with hygromycin resistance used to stably express HEXB beta chain, secretable alkaline phosphatase (SEAP) or a chimeric protein made as a fusion of granzyme B to *Gaussia* luciferase under the control of a chimeric hCMV-MoMLV 5'-LTR strong constitutive promoter (A) or Tetracycline Inducible Promoter (B).
Figure 3:
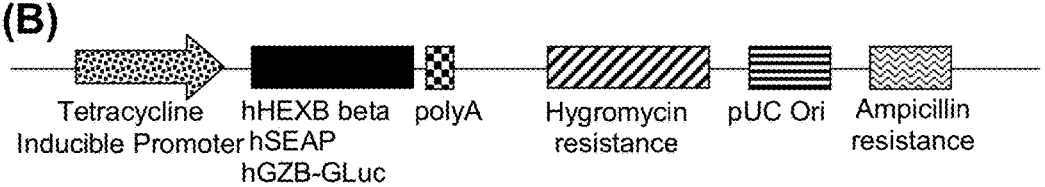

As cited above, the present invention relates to a cell based sensor useful for drug discovery, diagnostic and determination of analytes that comprises a cell line with professional regulated exocytosis of secretory granules overexpressing a non-protease hydrolase selected, preferably, from a group comprising: a *Gaussia* luciferase fusion protein with a granule targeting protein; a secretable alkaline phosphatase and a chain beta of beta-hexosaminidase, as possible reporter polypeptides, stored in the regulated secretory granules of the cell line with professional regulated exocytosis and having either an endogenous or a heterologous molecule as a modulator of regulated secretory granules exocytosis. Said granule stored non protease-hydrolase reporter having at least: a high resistance to conditions already present inside the granules, such as low pH and proteolysis by proteases; enzymatic activity after exocytosis; a highly specific substrate; absence of toxicity, specially after cell thawing; a very low level of secretion under unstimulated or basal conditions; and a high signal to background activity in a media compatible with cell culture viability and granule exocytosis for a high throughput robust and sensitive detection.

When the cell based sensor is incubated with a specific ligand of the exocytosis modulator, the reporter polypeptide is released from granules into the extracellular media and the enzymatic activity of such released reporter polypeptide is detected with a specific substrate.

The cell based sensor of the present invention thus comprises: a hematopoietic cell line with professional regulated exocytosis; a granule stored non-protease hydrolase reporter transfected and overexpressed into such said hematopoietic cell line and such granule stored reporter under the control of a suitable promoter; an exocytosis modulator for example a surface receptor, like a GPCR, under the control of a suitable promoter and a specific substrate for detection of the secreted granule stored non-protease hydrolase reporter.

Such sensitive cell based sensor is useful for testing interactions between at least two molecules, one acting as the exocytosis modulator and the other as the specific ligand of the exocytosis modulator. Examples of uses of such sensors are: to test interactions between molecules in drug discovery, to quantify molecules such as proteins for diagnostic and for detection of drugs or molecules in several samples for example in the food industry, in environmental samples and in the pharmaceutical industry.

The sensor of the present invention is highly sensitive and thus uses a lower amount of cells than currently available sensors, its response is faster than sensors based on inducible promoters, no lysis is needed for release of reporters, signal can be measured either in end-point mode or in kinetic mode, all reagents can be mixed and then read, no washing or stop steps are needed thus increasing throughput, a stable and high signal to background is obtained for a robust assay with low variability between interassay experiments and it shows absence of toxicity, especially after cell thawing.

The present invention demonstrates that other hydrolases, different to proteases, are not toxic when overexpressed inside granules when cells are thawed and that they allow the development of highly sensitive sensors. In particular, certain glycosidases such as the chain β of beta-hexosaminidase and phosphatases such as secretable alkaline phosphatase are stored in high levels inside granules of hematopoietic cells with professional regulated exocytosis and are detected by ligand induced exocytosis with a high signal to background ratio and with low interassay variability. In addition, the present invention also demonstrates that the above invention's specific embodiments can be generalized to other non protease-hydrolases not normally stored inside the granules that may be redirected to granules by means of granule targeting polypeptides. For example, *Gaussia* luciferase is a non protease-hydrolase not normally stored inside granules that can be redirected to granule by means of a granule targeting polypeptide such as inactive granzyme B, overexpressed and stored into the granules and released like beta-hexosaminidase by a ligand induced exocytosis. Thus, hematopoietic cells overexpressing non toxic non protease-hydrolases become sensitive cell-based sensors with low variability to measure exocytosis Thus, this invention is based on the discovery that non-protease hydrolases may be overexpressed without toxicity into the granules of mammalian cells with professional regulated exocytosis to produce highly sensitive cell based sensors useful to measure exocytosis with low variability.

The present invention benefits from a previous patent application PCT/EP2010/004619 and all the teachings related to cells, promoters, exocytosis modulators are incorporated herein by reference.

Cells Used in the Present Invention

The present invention relates to a cell based sensor useful for drug discovery, diagnostic and determination of analytes that comprises a cell line with professional regulated exocytosis of secretory granules transfected with a non-protease hydrolase as a reporter polypeptide stored in the regulated secretory granules of the cell line with professional regulated exocytosis and having either an endogenous or a heterologous molecule as a modulator of regulated secretory granules exocytosis, such said granule stored non-protease hydrolase reporter having at least: a high resistance to conditions already present inside the granules such as low pH and proteolysis by other proteases; enzymatic activity after exocytosis; non-toxicity specially after cell thawing; a highly specific substrate; a very low level of secretion under unstimulated or basal conditions; and a high signal to background activity in a media compatible with cell culture viability and granule exocytosis for a high throughput robust and sensitive detection.

Secretory granules and their regulated exocytosis are well known in the state of the art and have been most extensively studied in a few cell types chosen either as model systems due to certain experimental advantages or due to their crucial physiological or pathophysiological interest (see for example, Burgoyne, R D and Morgan, A. Physiological Reviews, Vol. 83, No. 2, April 2003, pp. 581-632). Probably the most studied cell types have been the adrenal chromaffin cell (and its tumor counterpart the PC12 cell line), the pancreatic beta-cell and hematopoietic cells like mast cells, platelets and neutrophils but secretory granule exocytosis also occurs, however, in many different neuroendocrine and endocrine cell types for the secretion of peptides and other hormones and in exocrine cells for the secretion of digestive enzymes. Moreover it has been demonstrated that even in non-professional secretory cell lines such as fibroblastoid cell lines (CHO cells) a Ca2+-regulated pathway for exocytosis exist and this probably all cell types might possess a regulated exocytotic pathway, that is, conventional lysosomes can be triggered by Ca2+ to undergo exocytosis. But secretory lysosomes are a distinct class of regulated secretory organelle and this exocytic capacity clearly marks them from conventional lysosomes. Although conventional lysosomes can also fuse with the plasma membrane and release their soluble contents following stimulation (1), the extent of Ca2+-triggered secretion of lysosomal enzymes from cells such as fibroblasts and epithelial cells tends to be only 10-20% (2). In comparison, up to 80% of lysosomal markers are released upon a physiological trigger from cells that possess secretory lysosomes, called herein, cells with professional regulated exocytosis. Thus, preferred cells for the methods of the present invention are selected from a group comprising cells with professional regulated exocytosis. One of the most diverse groups of cells with professional regulated exocytosis is that comprising hematopoietic cells like neutrophils, basophils, eosinophils, T-cells such as cytotoxic T lymphocytes and Natural Killer cells (NK cells). Central to the normal function of all the above cells is regulated exocytosis of vast amounts of stored components like hydrolases such as proteases, glycosidases and phosphatases. Thus, hematopoietic cells with professional regulated exocytosis are highly relevant cells for the methods of the present invention.

In one embodiment of the present invention the cells are selected from a group of hematopoietic cell lines with professional regulated exocytosis selected from cells such as cytotoxic T lymphocytes, neutrophils, mast cells, and basophils that use their secretory lysosomes to store specialized components such as hydrolases like glycosidases and phosphatases.

In another embodiment of the present invention preferred cells are selected from RBL-2H3, a rat basophilic leukaemia cell line, mouse 32D cell line, a mouse bone marrow hematopoietic cell, human NK92 cell line, a natural killer cell line and human YT cell line, a natural killer cell line and mouse MC/9 cell line, a mouse mast cell. Particularly preferred cell line for the methods of the present invention is RBL-2H3 because this cell line has a very low constitutive secretion level and highly induced secretion of preferred non-protease hydrolase reporters of the present invention like chain beta of beta-hexosaminidase, secreted alkaline phosphatase or a fusion protein between a *gaussia* luciferase and a granule targeting protein that renders a sensor with a high signal to background.

Exocytosis Modulators Used in the Invention

The present invention also comprises exocytosis modulators. In one embodiment of the present invention exocytosis modulators are selected from compounds or polypeptides that induce a change in the level of intracellular calcium. In another embodiment of the invention exocytosis modulators are selected from compounds or polypeptides that induce a change in the levels of cAMP, diacylglycerol (DAG), phospholipids, or ATP that in turn regulate or modulate calcium triggered exocytosis.

Granule Stored Reporters Used in the Invention

The most widely used reporter for granule secretion is endogenous beta-hexosaminidase but this protein, as used, expressed and disclosed in the state of the art, it has been traditionally considered a low sensitivity reporter with a low signal to background ratio and a strong variability between experiments due to a large variation over time in the amount of enzyme stored in the granules (see PCT/EP2010/004619). However, the present invention surprisingly demonstrates that the overexpression of chain beta of beta-hexosaminidase results in a sensor with low variability and a high signal to background. In addition, as explained above, overexpression of this glycosidase is not toxic to cells when thawing.

Sorting of soluble proteins between the constitutive and the regulated pathways is clearly complex, and there is substantial evidence for cell-type specificity in the routing of soluble proteins to storage granules, regardless of the level of expression. For example, amylase is a normal granule constituent in exocrine pancreatic cells, and is trafficked to granules when transfected into exocrine pancreatic cell lines but is constitutively secreted in transfected endocrine cell lines (see for example, El Meskini, R et al. Endocrinology (2001) Vol. 142, No. 2 864-873). Cell type specificity may explain some of the contradictory results using portions of the amino terminal of the POMC molecule to study routing in various endocrine and neuronal cell lines (see for example, Tam W W H et al. Eur J Cell Biol (1993), 62:294-306; Roy P et al. Mol Cell Endocrinol (1991), 82:237-250 and Cool D R et al. J Biol Chem (1995) 270:8723-8729. Cell specificity of protein sorting extends beyond cell lines to primary cultures, as the same constructs can be handled quite differently in primary endocrine and neuronal cells. Thus, for those skilled in the art, other cells different than hematopoietic cells with regulated exocytosis could be used in the methods of the present invention but the selection of other cell types need to be made in parallel with a specific reporter stored at high concentration in the secretory granules of the selected cell line and with a low level of basal secretion.

One important property of a reporter to be useful in the methods of the present invention stored in secretion granules, especially in secretion granules of cells of hematopoietic origin, is the resistance to the harsh environment this reporter most withstand inside the granules. Secretion granules of hematopoietic cells are related with lysosomes, organelles that store inside a vast pool of hydrolases such as cathepsins, tryptases and chymases at a very acidic pH and this environment is not ideal for a protein not naturally stored in such organelles, thus a reporter labile to proteases or a pH labile reporter will probably be degraded inside secretory granules thus lowering the sensitivity of such labile reporter protein. For example, proteases are the major protein constituent exocytosed from activated mast cells (see for example Huang et al, J Clin Immunol. 18:169-183, 1998). Tryptases, chymases, and carboxypeptidases are the three major families of proteases stored in the secretory granules of mast cells. Thus, preferred reporters of the present invention are polypeptides with a high resistance to proteolysis and low pH inside the granules of the hematopoietic cells of the present invention. Although the coexistence of lysosomal enzymes and hematopoietic serine proteases with several antibiotic proteins in secretory lysosomes indicates that co-storage is possible without degradation not every polypeptide artificially directed to secretory granules will resist this harsh environment. For example, Kaur J and Cutler D F (see Kaur, J and Cutler D F. J. Biol. Chem., (2002) Vol. 277, Issue 12, 10498-10505) have found that a chimeric HRP-Pselectin can be targeted to both secretory and conventional lysosomes but up to 70% of targeted protein was proteolytically degraded.

Secretory granules of hematopoietic cells used in the methods of the present invention share properties with lysosomes which are organelles that store inside a vast pool of hydrolases such as cathepsins, tryptases and chymases at a very acidic pH environment and thus useful reporters for the methods of the present invention must be polypeptides resistant to the environment inside granules of suitable hematopoietic cells.

In one embodiment of the present invention useful reporters are selected from polypeptides resistant to the environment inside the granules of hematopoietic cells, such as proteolysis and low pH.

Promoters for Reporter Expression

This invention also comprises suitable promoters for expression of reporters. Useful promoters for expression of granule stored reporters of the present invention are promoters suitable for protein expression in hematopoietic cells, in particular promoters suitable for medium to high protein expression. Another relevant property of suitable promoters is that protein expression must be stable during culture. Certain heterologous promoters are downregulated during culture especially in hematopoietic cells and this process is called "promoter silencing". Preferred promoters for the methods of the present invention are thus non-silenciable promoters.

Detection Technologies and Substrates

Besides resistance to environment inside secretory granules, high level expression, low basal secretion and high induced secretion of a reporter to be useful in the methods of the present invention, other important properties of reporters for regulated exocytosis for the sensitive detection methods of the present invention is type of detection technology used to measure the secreted reporter and the catalytic efficiency of such reporter for the specific substrate used for detection. Both highly sensitive detection technologies and a reporter with a high catalytic efficiency for a specific substrate are beneficial for the methods of the present invention.

In one embodiment of the present invention the substrate used to detect secreted non protease-hydrolase may be selected from a colorimetric, a fluorescent substrate or a chemiluminescent substrate. One example of substrate for HEXB is 4-Methylumbelliferyl N-acetyl-$\beta$-D-glucosaminide (4MU-NGlc) but other substrates for glycosidases may be synthesized and tested. Examples of substrates for phosphastases are 4-methylumbelliferyl phosphate and fluorescein diphosphate but other substrates for phosphastases may also be useful. Substrates for *gaussia* luciferase may be selected from coelenterazines and their derivatives.

Applications of the Cell Based Sensor of the Present Invention

Cell based sensors of the present invention are in general useful for testing interactions between at least two molecules, one acting as the exocytosis modulator and the other as the specific ligand of the exocytosis modulator. For example, in drug discovery thousands or even millions of small molecules are tested against a target to find small molecules that modify the activity of such target. In a particular example, compounds are screened for agonists or antagonist of G-protein coupled receptors, a highly drugable class of receptors. But the same sensor has applications in detection and quantitation of compounds that modulate granule exocytosis, for example, drugs of abuse in several samples for example in the food industry, environmental samples and for diagnosis. Uses of the sensor are not limited to either cell surface receptors or to small modulators of surface receptors. For example, with a pair of two molecules that bind to a protein to be determined, fast, specific and sensitive detection could be carried out by using the sensor of the present invention provided one of the molecules that bind to the protein to be determined is a specific immunoglobulin E and the other molecule that bind to the protein to be determined induces oligomerization of the protein to be determined. Other uses of the above sensor are for testing anti-allergic compounds and for detection of allergens.

Kits for Testing if a Compound Modulates Exocytosis

The present invention also comprises kits for testing if a compound modulates exocytosis. Such kit comprises at least: a hematopoietic cell line with professional regulated exocytosis transfected with at least a heterologous non protease-hydrolase reporter under the control of a suitable promoter and a specific substrate for detection of secreted heterologous protease reporter. In addition, the hematopoietic cell line with professional regulated exocytosis may be either transfected with a heterologous exocytosis modulator under the control of a suitable promoter, like a GPCR, a heterologous Fc gamma I receptor or a heterologous Fc epsilon I receptor, or an endogenous exocytosis modulator like the endogenous Fc epsilon receptor I (the IgE receptor) could be used. Kits using the IgE receptor as the exocytosis modulator may contain an IgE specific for the analyte to be determined and a second molecule to induce oligomerization of the analyte bound to IgE.

Therefore the first embodiment of the present invention refers to a cell based sensor that comprises:
  a. A hematopoietic cell line with regulated exocytosis of secretory granules;
  b. A granule stored non-protease hydrolase reporter transfected into the cell line of (a) and overexpressed under the control of either a strong constitutive promoter or a strong inducible promoter;
  c. An endogenous modulator or a transfected heterologous modulator of regulated exocytosis of the secretory granules of the cell line of (a);
  d. A cell impermeable substrate selected from the group comprising: a colorimetric, a fluorescent or a luminescent substrate specific for detection of a secreted non-protease hydrolase activity;

which allows measuring the effect of a specific ligand on the modulator of regulated exocytosis.

In a preferred embodiment the non-protease hydrolase is selected from secretable alkaline phosphatase (SEAP) of SEQ ID NO: 1, chain beta of beta-hexosaminidase (HEXB) (Gene Bank BC017378.2 with date 26 Jan. 2012) or a fusion protein between *Gaussia* luciferase (GLuc) and a granule targeting protein (SEQ ID NO: 2); the cells are selected from the group comprising: the rat basophilic leukaemia cell line RBL2H3, the mouse bone marrow hematopoietic cell line 32D, the natural killer cell line human NK92 cell line, the natural killer cell line human YT cell line and the mouse mast cell mouse MC/9 cell line; and the modulator of regulated secretory granules exocytosis is an endogenous surface receptor or a transfected heterologous surface receptor selected from the group comprising: G-protein coupled receptors (GPCR), receptors bearing an ITAM motif, receptors bearing an ITIM motif and protein tyrosine kinases receptors.

The second embodiment of the present invention refers to a method to obtain the above mentioned biosensor which comprises transforming a hematopoietic cell line bearing an endogenous modulator of regulated secretory granules exocytosis or bearing a transfected heterologous surface receptor under the control of a suitable promoter with a vector codifying for the granule stored reporter under the control of a suitable promoter. In a preferred embodiment the vector codifying for the modulator of regulated secretory granules exocytosis also comprises a signal peptide useful for receptors overexpression at the surface of cells, and/or a tag for surface detection and/or separation of positive cells.

In another preferred embodiment the promoter for constitutive overexpression of the modulator of regulated secretory granules exocytosis is selected from the group comprising mammalian elongation factor 1-alpha promoter (hEF1alpha) (SEQ ID NO: 3), and 5'LTR from Moloney Murine Leukaemia Virus promoter MoMLV-5'LTR (SEQ ID NO: 4). In another preferred embodiment the promoter useful for overexpression of the modulator of regulated secretory granules exocytosis is an inducible promoter selected from the group comprising tetracycline inducible promoter, ecdysone inducible promoter, cumate inducible promoter and progesterone inducible promoter.

In a still preferred embodiment the vector for overexpression of a modulator of regulated secretory granules exocytosis comprises a viral GPCR derived sequence (VGS) of SEQ ID NO: 5 or SEQ ID NO: 6 for surface overexpression.

In a still preferred embodiment the vector for constitutive overexpression of a modulator of regulated secretory granules exocytosis is P-MoMLV-5'LTR-SP-cmyc-tag-VGS-MCS-polyA (SEQ ID NO: 7).

In another preferred embodiment the promoter for strong constitutive overexpression of granule stored reporters is selected from the group comprising a chimeric promoter of hCMV and MoMLV-5'-LTR promoter (SEQ ID NO: 4); MoMLV-5'LTR promoter (SEQ ID NO: 4) and Elongation Factor 1-alpha promoter (SEQ ID NO: 3).

In a still preferred embodiment the granule stored reporter is overexpressed under the control of an inducible promoter selected from the group comprising tetracycline inducible promoter, ecdysone inducible promoter, cumate inducible promoter and progesterone inducible promoter.

The third embodiment of the present invention refers to a method of testing or to quantify interactions between at least two molecules, one acting as the exocytosis modulator and the other as the specific ligand of the exocytosis modulator, comprising the steps of:
a) Incubating the above described cell based sensor in a media compatible with cell viability, exocytosis and enzymatic activity of secreted granule stored reporters,
b) adding a specific ligand of exocytosis modulator,
c) adding a specific substrate of the granule stored reporter, and
d) detecting the non-protease hydrolase enzymatic activity of the reporter polypeptide, released from granules into the extracellular media, with a specific substrate of said released reporter.

The fourth embodiment of the present invention refers to the use of the above mentioned cell based sensor for detecting a protein to which a pair of two molecules bind to, wherein one of the molecules that bind to the protein to be detected is a specific immunoglobulin G, or a specific immunoglobulin E, or a specific immunoglobulin A and the second molecule that binds to the protein to be detected induces oligomerization of said protein to be detected, upon binding.

The fifth embodiment of the present invention refers to the use of the above cited cell based sensor for testing interactions between molecules in drug discovery or to quantify molecules such as proteins for diagnostic or for detection of drugs or molecules in samples of the food industry, in environmental samples and in the pharmaceutical industry, for testing IgE-allergen interactions, for testing anti-allergic compounds and/or for detecting allergens.

The sixth embodiment of the present invention refers to a kit comprising the above cited cell based sensor for testing if a compound modulates exocytosis or to quantify the extent of such exocytosis. In a preferred embodiment the kit comprises at least one specific substrate for detection of secreted heterologous reporter.

EXAMPLES

Example 1. Development of Stable Cell Lines Expressing Chain Beta of Human HEXB Under the Control of hCMV-MoLV5'LTR Chimeric Promoter Vectors were developed for stable expression of human beta chain of HEXB under the control of hCMV-MoLV5'LTR chimeric promoter. A hygromycin resistance cassette was included in the vector backbone for selection of stable populations of cells. The vector also included an IRES-NGFR cassette cloned downstream of human HEXB and thus, under the control of the same promoter for flow cytometry and/or selection of stable cells expressing HEXB.

Each vector was individually electroporated using a microporator (Digital Bio Technology, South Korea) into RBL-2H3 and after 48 hours hygromycin at 1500 ug/mL was added to culture for selection. After selection for about 2 weeks cells were analysed by flow cytometry (Guava Technologies, USA) with an antibody against NGFR coupled to FITC. Positive population where magnetically separated by MACS using anti-NGFR-MACS sup.R (Miltenyi Biotec, Germany). Sorted populations were again analysed by flow cytometry to check the sorting efficiency. Positive cells were cloned by limiting dilution at 0.3 cells per well of 96 well microplates. Wells with growing colonies were analysed for NGFR expression by flow cytometry. Three clones, named 1B7-HEXB, 1C4-HEXB and 1F10-HEXB with positive expression for NGFR were expanded to 6 well plates together with non-transformed RBL2H3 and the stably transfected whole population of cells (RBL2H3-HEXB).

Cells were harvested with pipette, centrifuged, resuspended in HBSS buffer, counted using a Neubauer chamber and adjusted to 500.000 cells per mL. The substrate used for determination of HEXB activity was 4-Methylumbelliferyl N-acetyl-β-D-glucosaminide (4MU-NGlc) (Sigma-Aldrich, M2133) and it was diluted in HBSS to 1 mM final concentration in the assay well.

A mouse IgE monoclonal antibody against trinitrophenyl hapten was purified from IgELb4 hybridoma purchased from ATCC (TIB-141) and was used to induce exocytosis through cross-linking of IgE receptor by IgE bound to TNP conjugated to BSA. TNP-N-hydroxysuccinimide ester was purchased from Biosearch Technologies Inc and conjugated to bovine serum albumin (BSA) using a standard protocol. Conjugation was determined at pH 7.0 by measuring TNP absorbance at 348 nm using 15400 units per mol per 10 mm light pass length as the extinction coefficient of TNP. Molar ratio of TNP to BSA in the TNP-BSA conjugate was 18:1 and was calculated assuming the molecular weight of BSA is 60000.

A 384 black wall microplate was used for assay. A first mix in HBSS of 2 micrograms per mL of IgELb4 IgE antibody and 2 micrograms per mL of TNP-BSA together with 2 mM of 4MU-NGlc was used to measure exocytosis. A second mix was used as control and it was only 2 mM of 4MU-NGlc without IgE and without TNP-BSA. Ionomycin was used as control at 10 uM. Wells without cells were used as blank. 10 microliters of cells (either 1B7-HEXB, 1C4-HEXB and 1F10-HEXB, non-transformed RBL2H3 and RBL2H3-HEXB) were added each to 12 wells. To six wells were added 10 microliters of the mix containing IgE+TNP-BSA plus 4MU-NGlc while for the other six wells only 4MU-NGlc was added. Plates were incubated at 37° C. and fluorescence was read at 360 nm excitation and 470 nm as emission wavelength in a BMG-Labtech Optima fluorescence reader. Read was taken at 0, 15, 30, 45 and 60 minutes. 30 minutes were selected as time for optimal results. The results at 30 min were as shown in the following Table 1:

TABLE 1

| CELLS | FLUORESCENCE (IgE + TNP-BSA, specific exocytosis) | FLUORESCENCE (No IgE + TNP-BSA, background release) |
|---|---|---|
| RBL2H3 | 6.424 +/− 584 | 2.056 +/− 30 |
| RBL2H3-HEXB (whole stable population) | 14.149 +/− 309 | 2.908 +/− 77 |
| 1C4-HEXB clone | 39.185 +/− 1.024 | 6.302 +/− 132 |
| 1F10-HEXB clone | 17.378 +/− 362 | 4.394 +/− 83 |
| 1B7-HEXB clone | 28.554 +/− 790 | 2.611 +/− 61 |
| No cells | 1.203 +/− 42 | 1.176 +/− 47 |

The above results indicate that overexpression of the beta chain of HEXB into RBL2H3 cells, produces a functional enzyme as measured with 4MU-NGlc that is stored inside the granules and specifically released by exocytosis. From the above data, specific and background release were calculated by subtracting the fluorescence of wells without cells. In the whole stably transfected population specific signal is increased 2.48 times with respect to parental RBL2H3 cells while background increased 1.97 times, that is, specific signal increased more than background release and this indicates that the uses of transfected cells as sensors is better than the use of parental cells. The specific signal to background (S/B) of RBL2H3 cells in this experiment was 5.9 times, while the S/B for RBL2H3-HEXB cells was 8.2 times. Clones selected by limiting dilution from the RBL2H3-HEXB whole population has increased specific release but also sometimes increased background release, as for example the clone 1C4-HEXB where the specific signal is increased 7.40 times with respect to RBL2H3 but background is increased 5.82 times with respect to RBL2H3. Thus, 1C4-HEXB clone has a S/B of 7.53 times. But clones like 1B7-HEXB has 1.63 times higher background than RBL2H3 and while the specific release is 5.24 times higher than that of RBL2H3. Thus, S/B of 1B7-HEXB clone is 19. Even more important is the fact that 1B7-HEXB production and release of HEXB is extremely regular while that of RBL2H3 has a very strong variability over time. Using the same conditions as above, both RBL2H3 and 1B7-HEXB were cultured for 2 months and exocytosis was measured as above every 1 month. Signal to background (S/B) of RBL2H3 was 5.9 (month 0), 2.8 (month 1) and 4.3 (month 2) while signal to background of 1B7-HEXB was 19 (month 0), 17 (month 1) and 22 (month 2). The above results confirm why exocytosis of RBL2H3 cells is always measured as a percentage for normalization of the strong natural variability that is observed in RBL2H3 cells (in the above results there was a reduction of 63% of S/B between month 0 and month 1). But 1B7-HEXB cells behave much better and the S/B while still variable as corresponds to live cells are more stable (in the above results the maximal variability was a 22% between month 2 and month 3).

Thus, the above results confirm that cells overexpressing the chain beta of HEXB are useful as sensors to measure exocytosis and that those sensors overexpressing HEXB are better than current state of the art sensors that comprise natural non-transfected RBL2H3 cells.

Example 2. Development of Stable Cell Lines Expressing Other Non Protease-Hydrolases Under the Control of hCMV-MoLV5'LTR Chimeric Promoter In order to demonstrate that overexpression of non protease-hydrolases is a general concept not restricted to HEXB, but that other proteins may redirected to granules and used to measure exocytosis vectors were developed for stable expression of human secretable alkaline phosphatase (SEAP) under the control of hCMV-MoLV5'LTR chimeric promoter and vectors were also developed for stable expression of Gaussia princeps luciferase cloned in frame as a fusion protein downstream of granzyme B, with serine at 193 mutated to alanine for inactivation of activity, used as a granule targeting protein (GZB-GLuc). A hygromycin resistance cassette was included in the vector backbone for selection of stable populations of cells. The vector also included an IRES-NGFR cassette cloned downstream of human SEAP or GZB-Luc and thus, under the control of the same promoter for flow cytometry and/or selection of stable cells expressing SEAP and/or GZB-GLuc.

Each vector was individually electroporated using a microporator (Digital Bio Technology, South Korea) into RBL-2H3 and after 48 hours hygromycin at 1500 ug/mL was added to culture for selection. After selection for about 2 weeks cells were analysed by flow cytometry (Guava Technologies, USA) with an antibody against NGFR coupled to FITC. Positive population where magnetically separated by MACS using anti-NGFR-MACS sup.R (Miltenyi Biotec, Germany). Sorted populations were again analysed by flow cytometry to check the sorting efficiency.

For SEAP, positive cells were cloned by limiting dilution at 0.3 cells per well of 96 well microplates. Wells with growing colonies were analysed for NGFR expression by flow cytometry. One clone, 2D1-SEAP was selected by both flow cytometry and SEAP activity using phosphatase substrate 4-MUP (Sigma-Aldrich, M3168). SEAP activity due to exocytosis was measured as in the example 1, that is, mixing 10 microliters of cells in suspension (5.000 cells) with 10 microliters of fluorescein diphosphate (Marker Gene Technologies, M1034) containing both IgELb4 and TNP-BSA. RBL2H3 cells were used as control and wells without cells were also used as blanks. Ionomycin was used as positive control.

Plates were incubated at 37° C. and fluorescence was read at 485 nm excitation and 535 nm as emission wavelength in a BMG-Labtech Optima fluorescence reader. Read was taken at 0, 15, 30, 45 and 60 minutes. 30 minutes were selected as time for optimal results. The results at 30 min were as in the following Table 2:

TABLE 2

| CELLS | FLUORESCENCE (IgE + TNP-BSA, specific exocytosis) | FLUORESCENCE (No IgE + TNP-BSA, background release) |
|---|---|---|
| RBL2H3 | 29.913 +/− 1.132 | 6.882 +/− 68 |
| 2D1-SEAP clone | 62.898 +/− 3.254 | 8.496 +/− 111 |
| NO CELLS | 5.982 +/− 42 | 6.142 +/− 54 |

The above results indicate that normally RBL2H3 cells produce high levels of phosphatase and that overexpression increases such levels as specific fluorescence at 30 minutes is 2.38 times higher in 2D1 clone than in RBL2H3 cells. Also background is increased and is 3.18 times higher in 2D1 than in RBL2H3 cells. In fact, in the above experiment S/B is better in RBL2H3 cells (S/B=32.3) than in 2D1 cells (S/B=24.2). But when S/B is measured over the course of 60 days, the S/B of 2D1 was almost constant (S/B=25.1 at month 1 and 24.9 at month 2) while S/B for RBL2H3 was highly variable (S/B=17.9 at month 1 and 5.34 at month 2). The above results illustrate the fact that the effect of protein overexpression is not only to increase the amount of enzymes stored into the granules but also to reduce the variability normally associated with exocytosis in RBL2H3, and thus, better sensors may be developed by overexpressing non protease-hydrolases into granules of cells with professional exocytosis. This example also indicates that an enzyme not normally stored into granules such as secretable alkaline phosphatase that is secreted in other cell lines like HEK293, Jurkat and CHO-K1 cells may be naturally stored inside the granules when transfected into cells with professional exocytosis.

In order to further expand the general concept that overexpression of non protease-hydrolases produces better sensors, the vector for expression of *Gaussia* luciferase cloned in frame downstream of human granzyme B, inactivated by mutation of serine at 193 to alanine, was transfected into RBL2H3 and cells were selected with hygromycin. Normally *Gaussia* luciferase is a secretable enzyme even when transfected alone into RBL2H3 cells (data not shown). But when fused to granzyme B, *gaussia* luciferase was stored into granules. A similar vector but using firefly luciferase fused downstream of granzyme B produced no luciferase activity into either supernatant or media from exocytosis (data not shown), indicating that enzymes that may be stored into the granules must be enzymes that resist the intracellular media with low pH and several proteases that is present inside such granules. The whole population of GZB-GLuc transfected cells was 56% positive for NGFR. As the signal of *gaussia* luciferase is a flash (not a stable signal) the exocytosis was made for 30 minutes using either IgELb4 and TNP-BSA or BSS alone and the supernatant corresponding to 100.000, 50.000, 25.000 and 12.500 cells was incubated into a 384 black wall plate with coelenterazine native at 16.6 micromolar final concentration as substrate (Biosynth AG, C-7000). Assay buffer was 10 mM Tris-HCl pH=7.8, 1 mM EDTA and 600 mM NaCl. Results were measured with a Fluoroskan Ascent FL from Thermo Labsystems. See Table 3.

TABLE 3

| CELLS | LUMINESCENCE (IgE + TNP-BSA, specific exocytosis) | LUMINESCENCE (No IgE + TNP-BSA, background release) |
|---|---|---|
| 100.000 GZB-GLuc | 6.281 | 534 |
| 50.000 GZB-GLuc | 4.707 | 213 |
| 25.000 GZB-GLuc | 3.775 | 137 |
| 12.500 GZB-GLuc | 997 | 71 |
| NO CELLS | 24.2 | 28.6 |

The above results demonstrate that non protease-hydrolases not normally stored into granules of cells with professional regulated exocytosis may be artificially redirected to granule by using a granule targeting polypeptide such as granzyme B and that such granule stored non protease-hydrolases produce useful sensors to measure exocytosis. Using 12.500 cells the signal to background was 22.94. Thus, overexpression of non protease-hydrolases inside the granules produces sensors that are better to measure exocytosis than current available sensors.

Example 3. Freezing and Thawing of Cell Lines Overexpressing Non Protease-Hydrolases Inside the Granules This example has been designed to demonstrate the stability of sensors bearing different non protease-hydrolases. 1B7-HEXB clone, 2D1-SEAP clone, RBL2H3 parental cells and RBL2H3-GRZB were frozen at 4 millions of cells per cryotube in 1 mL of freezing media (cell culture media+10% DMSO). Cells were frozen in a Cryo Freezing container "Mr Frosty" (Nalgene, now Thermo, 5100-0001) with isopropyl alcohol and a −80° C. freezer for 24 hours and then were stored into vapour phase of liquid nitrogen. Thawing was made as follows: the cryotube was placed in a water bath at 37° C. until cells were thawed and 9 mL of culture medium were added to each vial of cells. Cells were then centrifuged and viability was determined by trypan exclusion. Cells were cultured and viability after 24 hours of culture was again estimated as healthy viable cells were adherent while detached cells were non-healthy. The results were as follows: the viability immediately post thawing was over than 95% for 1B7-HEXB, 2D1-SEAP and RBL2H3 and cells were brilliant and membranes regular and round. The viability of RBL2H3-GRZB was over than 90% but about 30-40 percent of the cells present irregular bulges in the plasma membrane indicative of early apoptosis. In fact, over than 90% of the cells of 1B7-HEXB, 2D1-SEAP and RBL2H3 were attached to the bottom of plastic culture flasks (a measure of cell health) and alive while about 30-40% of RBL2H3-GZB cells died and in suspension. As matter of fact, the level of cell attachment to the flask is an indication of cell survival (viability) rate. This example, illustrates the fact than non-protease hydrolases have lower toxicity than protease hydrolases, when cells were thawed and that they have an advantage over proteases for the development of sensitive and stable sensors.

The invention claimed is:

1. A cell based sensor that comprises:
   a. A hematopoietic cell line with regulated exocytosis of secretory granules;
   b. A granule stored non-protease hydrolase reporter transfected into the cell line of (a) and overexpressed under the control of either a strong constitutive promoter or a strong inducible promoter;
   c. A modulator of regulated exocytosis of the secretory granules of the cell line of (a), wherein the modulator is an endogenous surface receptor or a transfected heterologous surface receptor, wherein the modulator is selected from the group consisting of: G-protein coupled receptors (GPCR), receptors bearing an ITAM motif, receptors bearing an ITIM motif, and protein tyrosine kinases receptors;
   d. A cell impermeable substrate selected from the group comprising: a colorimetric, a fluorescent or a luminescent substrate specific for detection of a secreted non-protease hydrolase activity;
   which allows measuring the effect of a specific ligand on the modulator of regulated exocytosis.

2. The cell based sensor, according to claim 1, wherein the non-protease hydrolase reporter is selected from the group consisting of secretable alkaline phosphatase (SEAP) of SEQ ID NO: 1, chain beta of beta-hexosaminidase (HEXB) (Gene Bank BC017378.2), and a fusion protein between *Gaussia* luciferase (GLuc) and a granule targeting protein (SEQ ID NO: 2).

3. The cell based sensor of claim 1 wherein the cells are selected from the group consisting of: the rat basophilic leukaemia cell line RBL2H3, the mouse bone marrow hematopoietic cell line 32D, the natural killer cell line human NK92 cell line, the natural killer cell line human YT cell line, and the mouse mast cell mouse MC/9 cell line.

4. The cell based sensor of claim 1 wherein the modulator consists of G-protein coupled receptors (GPCR).

5. A method to obtain the biosensor of claim 1 which comprises transforming the hematopoietic cell line bearing (i) an endogenous modulator of regulated secretory granules exocytosis or (ii) a transfected heterologous surface receptor in a vector under the control of a suitable promoter, with a vector codifying for the granule stored reporter of claim 1 under the control of either the strong constitutive promoter or the strong inducible promoter.

6. The method of claim 5, wherein the vector of the heterologous surface receptor (ii) also comprises a signal peptide useful for receptors overexpression at the surface of cells, or a tag for surface detection or separation of positive cells.

7. The method of claim 5 wherein the suitable promoter of the heterologous surface receptor (ii) is a constitutive promoter selected from the group consisting of mammalian elongation factor 1-alpha promoter (hEF1alpha) (SEQ ID NO: 3), and 5'LTR from Moloney Murine Leukaemia Virus promoter MoMLV-5'LTR (SEQ ID NO: 4).

8. The method of claim 5 wherein the suitable promoter of the heterologous surface receptor (ii) is an inducible promoter selected from the group consisting of tetracycline inducible promoter, ecdysone inducible promoter, cumate inducible promoter, and progesterone inducible promoter.

9. The method of claim 5 wherein the vector for expression of the heterologous surface receptor (ii) comprises a viral GPCR derived sequence (VGS) of SEQ ID NO: 5 or SEQ ID NO: 6 for surface overexpression.

10. The method of claim 5 wherein the vector for expression of the heterologous surface receptor (ii) is P-MoMLV-5'LTR-SP-cmyc-tag-VGS-MCS-polyA (SEQ ID NO: 7).

11. The method of claim 5 wherein the strong constitutive promoter of the granule stored reporter is selected from the group consisting of a chimeric promoter of hCMV and MoMLV-5'-LTR promoter (SEQ ID NO: 4); MoMLV-5'LTR promoter (SEQ ID NO: 4); and Elongation Factor 1-alpha promoter (SEQ ID NO: 3).

12. The method of claim 5 wherein the strong inducible promoter of the granule stored reporter is selected from the group consisting of tetracycline inducible promoter, ecdysone inducible promoter, cumate inducible promoter, and progesterone inducible promoter.

13. A method of testing or detecting interactions between at least two molecules, one acting as the exocytosis modulator and at least one other acting as a specific ligand of the exocytosis modulator, comprising the steps of:
   a. Incubating the cell based sensor of claim 1 in a media compatible with cell viability, exocytosis and enzymatic activity of secreted granule stored reporters,
   b. Adding a specific ligand of exocytosis modulator,
   c. Detecting the non-protease hydrolase enzymatic activity of the reporter polypeptide, released from granules into the extracellular media, with the specific substrate of said released reporter.

14. The method, according to claim 13, wherein the at least one other molecule acting as a specific ligand of the exocytosis modulator is a specific immunoglobulin G, a specific immunoglobulin E, or a specific immunoglobulin A, and induces oligomerization of the exocytosis modulator upon its binding to the exocytosis modulator.

15. A kit comprising the cell based sensor of claim 1.

* * * * *